(12) United States Patent
Carls et al.

(10) Patent No.: US 8,317,832 B2
(45) Date of Patent: Nov. 27, 2012

(54) IMPLANTS AND METHODS FOR INTER-SPINOUS PROCESS DYNAMIC STABILIZATION OF SPINAL MOTION SEGMENT

(75) Inventors: Thomas Carls, Memphis, TN (US); Eric C. Lange, Collierville, TN (US); Kent M. Anderson, San Jose, CA (US); Jean Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/369,378

(22) Filed: Feb. 9, 2012

(65) Prior Publication Data
US 2012/0136391 A1    May 31, 2012

Related U.S. Application Data

(63) Continuation of application No. 12/050,274, filed on Mar. 18, 2008, now Pat. No. 8,114,136.

(51) Int. Cl.
*A61B 17/70* (2006.01)
*A61B 17/88* (2006.01)

(52) U.S. Cl. ......... 606/249; 606/246; 606/248; 606/279

(58) Field of Classification Search .......... 606/246–279; 623/17.11–17.16
See application file for complete search history.

(56) References Cited

U.S. PATENT DOCUMENTS

| | | | |
|---|---|---|---|
| 624,969 A | 5/1899 | Peterson | |
| 1,153,797 A | 9/1915 | Kegreisz | |
| 1,516,347 A | 11/1924 | Pataky | |
| 1,870,942 A | 8/1932 | Beatty | |
| 2,077,804 A | 4/1937 | Morrison | |
| 2,299,308 A | 10/1942 | Creighton | |
| 2,485,531 A | 10/1949 | Dzus et al. | |
| 2,607,370 A | 8/1952 | Anderson | |
| 2,677,369 A | 5/1954 | Knowles | |
| 2,685,877 A | 8/1954 | Dobelle | |
| 3,065,659 A | 11/1962 | Eriksson et al. | |
| 3,108,595 A | 10/1963 | Overment | |
| 3,397,699 A | 8/1968 | Kohl | |

(Continued)

FOREIGN PATENT DOCUMENTS

DE    2821678 A1    11/1979

(Continued)

OTHER PUBLICATIONS

Anasetti et al., "Spine Stability After Implantation of an Interspinous Device: An In Vitro and Finite Element Biomechanical Study," J. Neurosurg. Spine, Nov. 2010, vol. 13, pp. 568-575.

(Continued)

*Primary Examiner* — Alvin Stewart
*Assistant Examiner* — Nicholas Plionis
(74) *Attorney, Agent, or Firm* — Sorell, Lenna & Schmidt, LLP (57) ABSTRACT

An implant assembly for stabilizing a spinal motion segment includes a spacer which is at least partially flexible and positionable in an interspinous spacer between adjacent spinous processes. The spacer member includes upper and lower surfaces structured to receive a respective adjacent one of the upper and lower spinous processes of the spinal motion segment and a body having distinctive first and second sections with differing flexibility to modify the manner of movement at the spinal motion segment.

13 Claims, 5 Drawing Sheets

U.S. PATENT DOCUMENTS

| | | |
|---|---|---|
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,035,712 A | 7/1991 | Hoffman |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,540,689 A | 7/1996 | Sanders et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,391 A | 12/1997 | Lin |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,749,916 A | 5/1998 | Richelsoph |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,527,803 B1 | 3/2003 | Crozet et al. |
| 6,554,833 B2 | 4/2003 | Levy |
| 6,572,653 B1 | 6/2003 | Simonson |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |

| Patent/Publication | Date | Name |
|---|---|---|
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,641,673 B2 | 1/2010 | Le Couedic et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2001/0049527 A1 | 12/2001 | Cragg |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0265074 A1 | 11/2006 | Krishna et al. |
| 2006/0271044 A1 | 11/2006 | Petrini et al. |
| 2006/0271049 A1 | 11/2006 | Zucherman et al. |
| 2006/0271061 A1 | 11/2006 | Beyer et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0050032 A1* | 3/2007 | Gittings et al. ............ 623/17.12 |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |

| | | |
|---|---|---|
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233084 A1 | 10/2007 | Betz et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0172090 A1 | 7/2008 | Molz |
| 2008/0177306 A1 | 7/2008 | Lamborne et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0243250 A1 | 10/2008 | Seifert et al. |
| 2008/0262617 A1 | 10/2008 | Froehlich et al. |
| 2008/0281359 A1 | 11/2008 | Abdou |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0264927 A1 | 10/2009 | Ginsberg et al. |
| 2009/0270918 A1 | 10/2009 | Attia et al. |
| 2009/0292316 A1 | 11/2009 | Hess |
| 2009/0326538 A1 | 12/2009 | Sennett et al. |
| 2010/0036419 A1 | 2/2010 | Patel et al. |
| 2010/0036424 A1 | 2/2010 | Fielding et al. |
| 2010/0121379 A1 | 5/2010 | Edmond |
| 2010/0145388 A1 | 6/2010 | Winslow et al. |
| 2010/0168795 A1 | 7/2010 | Winslow et al. |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |
| 2011/0054531 A1 | 3/2011 | Lamborne et al. |
| 2011/0144692 A1 | 6/2011 | Saladin et al. |
| 2011/0166600 A1 | 7/2011 | Lamborne et al. |
| 2011/0172708 A1 | 7/2011 | Fielding et al. |
| 2011/0295322 A1 | 12/2011 | Fielding et al. |

FOREIGN PATENT DOCUMENTS

| | | |
|---|---|---|
| DE | 3922044 A1 | 2/1991 |
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Bellini et al., "Biomechanics of the Lumbar Spine After Dynamic Stabilization," J. Spinal Discord Tech., 2006, vol. 00, No. 00, pp. 1-7.

Benzel et al., "Posterior Cervical Interspinous Compression Wiring and Fusion for Mid to Low Cervical Spinal Injuries," J. Neurosurg., Jun. 1989, ppp. 893-899, vol. 70.

Bini et al., "Minimally Invasive Treatment of Moderate Lumbar Spinal Stenosis with the Superion® Interspinous Spacer," The Open Orthopaedics Journal, May 27, 2011, pp. 361-367, vol. 5.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervértebral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Muller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Phillips et al., "Biomechanics of Posterior Dynamic Stabizing Device (DIAM) After Facetectomy and Disectomy," The Spine Journal, 2006, vol. 6, pp. 714-722.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lonnbaire Souple," Instabilité Vertebrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Device for Intervertebral Assisted Motion: Technique and Intial Results," 22 Neurosurg. Focus, Jan. 2007, vol. 22, No. 1, pp. 1-6.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

IMPLANTS AND METHODS FOR INTER-SPINOUS PROCESS DYNAMIC STABILIZATION OF SPINAL MOTION SEGMENT

This application is a continuation of prior U.S. patent application Ser. No. 12/050,274, filed Mar. 18, 2008, the disclosure of which is incorporated herein by reference in its entirety.

BACKGROUND

Implants can be positioned between adjacent spinous processes to provide resistance to vertebral movement as a result of extension of the spinal column. These implants can provide a shock absorber or bumper that dynamically limits spinal extension. The implants can be secured to the adjacent spinous processes with looped cables or straps that extend completely about the spinous processes and implant to maintain positioning of the implant between the spinous processes while also limiting spinal flexion. However, in addition to controlling the range of motion between adjacent spinal motion segments, it has been discovered that more positive patient outcomes also rely on changing the manner in which the adjacent spinal motion segments move relative to each other. Thus, there remains a need for an implant which can both control motion and alter the manner in which the spinal motion segments move.

SUMMARY

There is provided spinal implants, implant assemblies and methods that provide stabilization of a spinal motion segment through the posterior vertebral elements.

According to one aspect, a spinal implant includes a spacer member which extends along a longitudinal axis between opposite upper and lower ends. The upper and lower ends are structured to receive a respective one of the adjacent upper and lower spinous processes of a spinal motion segment. The spacer member includes a body including at least a first and a second section. Each of the first and second sections includes a flexibility characteristic that is different from the other.

According to another aspect, a spinal implant includes a spacer sized and shaped to extend between adjacent upper and lower spinous processes of a spinal motion segment. The spacer member includes a body with an exterior wall extending between opposite upper and lower ends. In an implantation orientation between the upper and lower spinous processes, the exterior wall includes an anterior surface opposite a posterior surface. The body further includes at least a first section having a first flexibility characteristic quality and a second section having a second flexibility characteristic that differs from the first flexibility characteristic. In one form, the first and second sections are configured to modify the manner of movement of the spinal motion segment when implanted between spinous processes of the adjacent vertebrae.

According to a further aspect, a method for stabilizing a spinal motion segment comprises: providing a spacer member including an upper end structured to contact an inferior surface of the upper spinous process and a lower end structured to contact a superior surface of the lower spinous process and a body including at least flexibly distinctive first and second sections, with the first section being less flexible than the second section; and positioning the spacer member between the adjacent upper and lower spinous processes of the spinal motion segment with the first section oriented anteriorly.

These and other aspects will be discussed further below.

BRIEF DESCRIPTION OF THE DRAWINGS

FIG. 4 is a sectional view of the spacer member of FIGS. 1 and 2 taken along view line 4-4 in FIG. 2.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Implants are positionable between adjacent spinous processes of a spinal motion segment to dynamically stabilize and limit spinal extension and/or flexion while altering the manner of movement between adjacent vertebral bodies which in one form includes repositioning the center of rotation for one or both of flexion and extension movement at the spinal motion segment. The implant includes a spacer member that forms a composite structure received between the spinous processes. The implant includes at least a first section and a second section with a flexibility characteristic that differs from that of the first section. In one form, the configuration of the first and second sections provides an asymmetry of flexibility between anterior and posterior sides of the implant that provides preferential deformation and influences the repositioning of the centers of rotation for flexion and extension at the spinal motion segment. In another form, the spacer member may be employed alone or with other implants, such as rods, plates, tethers, interbody fusion devices, interbody spacers, artificial discs, annulus repair system, or staples, for example.

In a further form, one or more engaging members in the form of a tether couples the implant to one or more posterior vertebral elements or implants. The engaging members can be engaged to the spacer member, or extend through the spacer member. The engaging members can be engaged to the posterior elements in a configuration that at least partially limits spinal flexion. Alternatively or additionally, the engaging members can be engaged to the posterior elements in a manner that prevents or resists the spacer member from being displaced from its implantation location between the spinous processes. In yet another form, the engaging members may increase the rigidity of one or more of the first and second sections.

Figure 1:
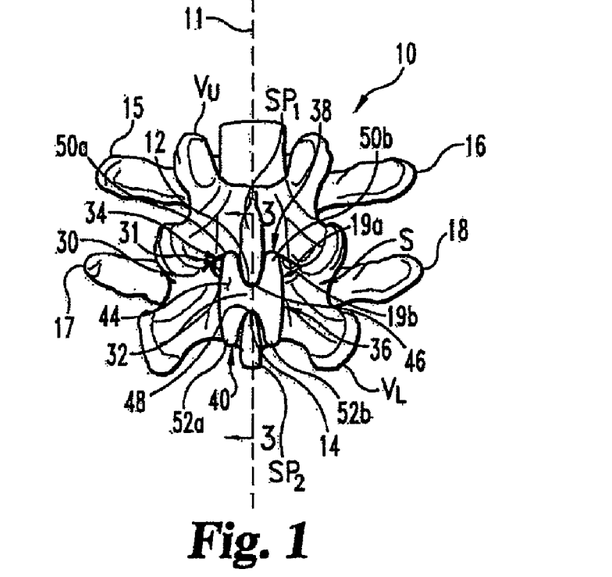
FIG. 1 is an elevation view of a posterior portion of a spinal column motion segment with a spinal implant in the form of a spacer member engaged therewith.
Figure 2:
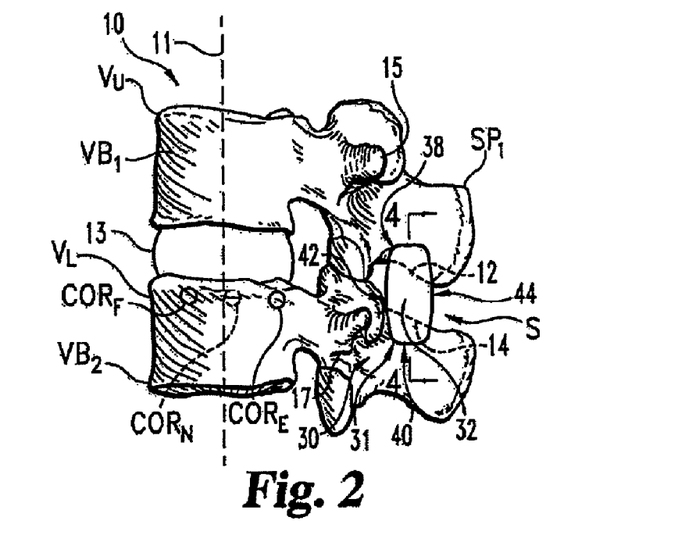
FIG. 2 is a lateral view of the spinal column motion segment of FIG. 1.

In FIGS. 1 and 2 there is shown a spinal column segment 10 including an upper vertebra $V_U$, a lower vertebra $V_L$ and a spinal disc 13 therebetween along a central axis 11 of the spinal column. The vertebrae $V_U$, $V_L$ and disc 13 comprise a spinal motion segment, it being understood that a spinal motion segment may include multiple vertebral levels in one more of the lumbar, thoracic, and cervical regions of the spine. Upper vertebra $V_U$ includes an upper spinous process $SP_1$ while the lower vertebra $V_L$ includes a lower spinous process $SP_2$, with the spinous processes $SP_1$, $SP_2$ defining a space S therebetween. The spinous processes $SP_1$ and $SP_2$ comprise posterior elements of the vertebrae $V_U$, $V_L$ of the spinal motion segment along with the transverse processes 15, 16, 17, and 18, laminae 19a, 19b, facets, pedicles and other posterior structures of each vertebrae $V_U$, $V_L$.

A spinal implant 30 in the form of a spacer member 31 is positioned in the space S and extends between and engages with the spinous processes $SP_1$, $SP_2$ to provide stabilization and modification of the spinal motion segment. Spacer member 31 includes a body 32 which in its implanted orientation has a first lateral side 34 and a second lateral side 36, with the lateral sides 34, 36 extending between a superior end 38 and an inferior end 40. As best seen in FIG. 2, for example, the body also includes an anterior side 42 opposite a posterior side 44. It should be appreciated that the transition between each of the anterior and posterior sides 42, 44, lateral sides 34, 36, and superior and inferior ends 38, 40 may be rounded or beveled in order to decrease the profile of the body 32 and minimize intrusion and potential trauma to adjacent neural tissue and surrounding spinal anatomy.

The body 32 further includes a first concave portion 46 and a second concave portion 48 situated at respective superior and inferior ends 38, 40. Each of the concave portions 46, 48 is disposed between a pair of respective upright arms 50a, 50b and 52a, 52b. Concave portions 46, 48 are sized and shaped to engage with and receive respective inferior surface 12 of the upper spinous process $SP_1$ and superior surface 14 of the lower spinous process $SP_2$. The arms 50a, 50b, 52a, and 52b extend beyond the respective concave portions 46, 48 to engage with the lateral sides of the spinous processes $SP_1$, $SP_2$. While concave portions 46, 48 are illustrated having a substantially arcuate shape, it should be appreciated that in one or more forms the concave portions 46, 48 may include an alternative configuration, such as a rectangular shape or may be structured to receive a greater portion of the spinous processes $SP_1$, $SP_2$ to further resist dislodgement from space S.

As illustrated in FIG. 2, the upper vertebra $V_U$ and lower vertebra $V_L$ have a normal center of rotation $COR_N$ (illustrated in phantom) for flexion and extension motion of the spinal motion segment when the spacer member 31 is not positioned in space S between the spinous processes $SP_1$, $SP_2$. While the normal center of rotation $COR_N$ is located substantially in the center of the vertebral bodies $VB_1$, $VB_2$ in FIG. 2, it should be appreciated that the position of the normal center of rotation $COR_N$ may vary based on several factors, including the region of the spinal column, individual patient anatomy, disease state or the effects of concurrent procedures (such as spinal decompression), just to name a few. Also illustrated in FIG. 2 are the resultant positions for the center of rotation for flexion $COR_F$ and the center of rotation for extension $COR_E$ when one form of spacer member 31 according to the present application is inserted in space S between the spinous processes $SP_1$, $SP_2$. In this form, the center of rotation for flexion $COR_F$ is repositioned anterior to the normal center of rotation $COR_N$ while the center of rotation for extension $COR_E$ is repositioned posterior to the normal center of rotation $COR_N$. Further details in regard to modifying the normal center of rotation $COR_N$ will be set forth below.

Figure 3A:
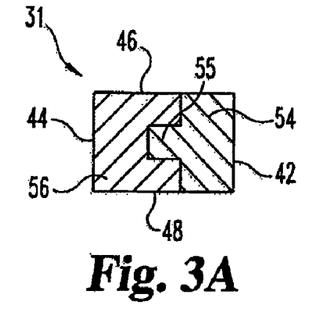
FIGS. 3A-3G are sectional views taken along view line 3-3 of FIG. 1 of various alternative embodiment spacer members.

Referring now to FIG. 3A there is shown a sectional view of one embodiment spacer member 31 along line 3-3 of FIG. 1. In this embodiment, the spacer member includes a first section 54 adjacent to anterior side 42 and a second section 56 positioned adjacent to posterior side 44 and abutting against first section 54, with each of the sections 54, 56 extending longitudinally between the spinous processes $SP_1$, $SP_2$. A portion of first section 54 is surrounded, at least along its superior and inferior sides, with second section 56. First and second sections 54, 56 form an overlapping arrangement in the anterior-posterior directions that provides a transition in the stiffness profile where the stiffness decrease posteriorly. First section 54 includes a posterior portion 55 that extends part-way into second section 56 in the anterior to posterior direction.

In this and the other forms contemplated herein, the spacer member 31 is fabricated from components that are flexible or exhibit at least some flexibility with the second section 56 being more flexible than the first section 54. Additionally, at least a portion of the spacer member 31 is resilient and/or elastic so it can assume various shapes during and after insertion and attachment. In one form, the flexibility of one or both of sections 54 and 56 is controlled by constructing the spacer member 31 with longitudinal gradations. In another form, the flexibility of the sections 54, 56 is varied by using materials with different elasticity, flexibility, or rigidity qualities. In one form, it is contemplated that the materials for the first section 54 and the second section 56 are selected based upon their modulus of elasticity.

It should be appreciated that either of sections 54, 56 may comprise any biocompatible material, material of synthetic or natural origin, and material of a resorbable or non-resorbable nature so long as the flexibility of the sections varies. For example, in one form of the present application, section 54 comprises PEEK while section 56 comprises silicone. It is also contemplated that other polymers such as ultra-high molecular weight polyethylene, polyaryletherketone, polyacetal, polysulfone, polyimide, polyester, polyvinyl alcohol, polyacrylonitrile, polytetrafluorethylene, polyparaphenylene, terephthalamide, cellulose, biocompatible rubber materials, and combinations thereof may be used. Suitable ceramic materials may include alumina, zirconia, polycrystalline diamond compact, pyrolitic carbon, and porous tantalum material. Suitable composite materials may include carbon-filled composites, hydroxyl-appetite-filled composites, and bioactive-glass-filled composites. The spacer member 31 may also include autograft, allograft or xenograft material and tissue materials including soft tissues, connective tissues, demineralized bone matrix and combinations thereof. In an embodiment including a resorbable material, any one or more of polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof may be a suitable material. It should be appreciated that the selection of material for one or both of sections 54, 56 will influence the positioning of the centers of rotation for flexion and extension $COR_F$, $COR_E$.

When spacer member 31 is inserted into the space S each of the spinous processes $SP_1$, $SP_2$ bears against the first section 54 and the more flexible second section 56. Since the spinous processes bear against both sections 54 and 56, a preferential deformation of the spacer member 31 is formed by movement of the spinal motion segment and the centers of rotation for flexion and extension $COR_F$, $COR_E$ are influenced. When the more rigid section 54 is disposed anterior to the second section 56 and the spinal motion segment undergoes extension, the center of rotation for extension $COR_E$ is moved posterior to the normal center of rotation $COR_N$ because the spinous processes $SP_1$, $SP_2$ rotate about the more rigid section 54 and compress or deform the more flexible second section 56 as they move toward one another. As the spinal motion segment undergoes flexion movement, the spinous processes $SP_1$, $SP_2$ again rotate about the more rigid section 54 until enough force is created to compress or deform section 54, thus repositioning the center of rotation for flexion $COR_F$ anterior to the normal center of rotation $COR_N$. Moreover, when the more rigid section 54 is placed anterior to the second section 56, section 54 is provided with sufficient rigidity in one embodiment to maintain a distraction distance between the laminae 19a, 19b in order to avoid stenosis and associated neural complications.

Referring now generally to each of FIGS. 3B-3G there is illustrated a sectional view of alternative embodiment spacer members 31b-31g. It should be understood that the configuration of each of the spacer members 31a-31g has been varied by adjusting the positioning of the first section 54 relative to the second section 56 in order to provide spacer members with alternative flexibility characteristics which may be used to alternatively vary or control movement of the spinal motion segment.

Figure 3B:
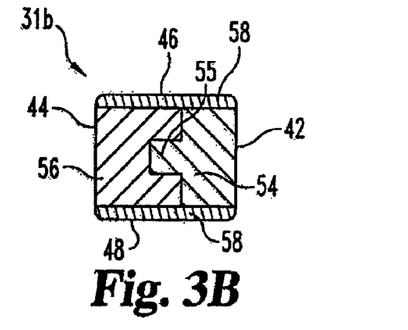
Figure 3C:
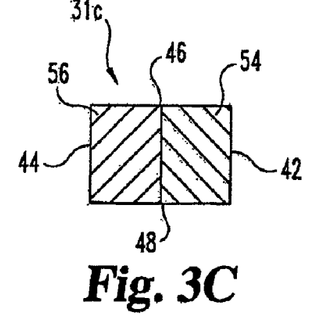
Figure 3D:
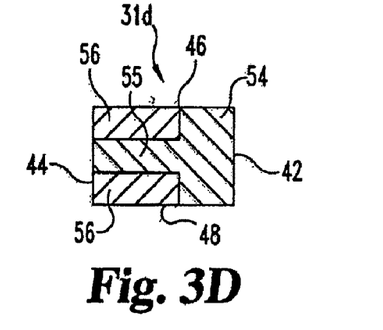

Referring to FIG. 3B, spacer member 31b further includes a third section 58 which comprises a material generally more flexible than the material of sections 54, 56. The material of section 58 is generally structured to conform to the respective adjacent spinous process $SP_1$ or $SP_2$ in order to provide enhanced reception and engagement and may comprise one or more of the materials suitable for sections 54 and 56. For example, in FIGS. 3C and 3D the spacer members 31c and 31d will react much the same as spacer 31 during flexion and extension. In FIG. 3C, first section 54 and second section 56 are arranged in side-by-side relation to one another in the anterior-posterior direction with no overlapping portions. In FIG. 3D, first section 54 includes a posterior extension 55 that is surrounded at least one its superior and inferior sides with second section 56, and extension 55 extends to the posterior side 44.

Figure 3E:
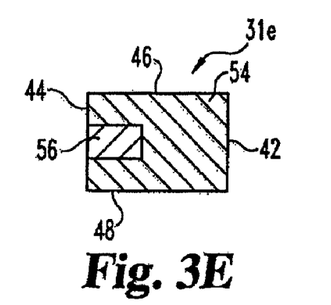
Figure 3F:
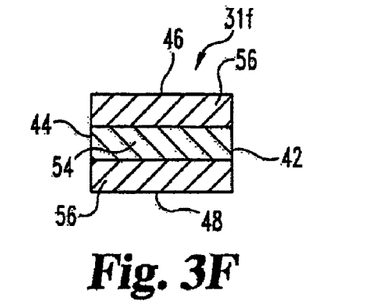
Figure 3G:
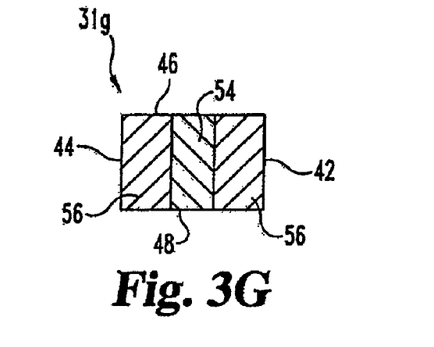

In FIG. 3E, the first section 54 is disposed both superiorly and inferiorly around the second section 56, such that the first section 54 creates an axial force which compresses the second section 56 during extension of the spinal motion segment. Moreover, in FIG. 3F the first section 54 of spacer member 31f is at least partially surrounded by the second section 56 such that the first section 54 will limit the flexibility of the second section 56 when a force greater than the elastic or compressive limit of section 56 is applied thereto. In FIG. 3G, first section 54 is surrounded at least partially along its anterior and posterior sides with a more flexible second section 56. Spacer 31g will provide deformation of the second section 56 during both spinal extension and spinal flexion, while first section 54 provides resistance to deformation when the supported vertebrae are in their neutral position.

In the embodiments discussed above, the arrangement of the first and second sections can be reversed so that the first section 54 is more flexible than the second section 56. Still other embodiments contemplate more than first and second sections to provide additional gradations in the flexibility of the implant. In still other embodiments, it is contemplated that one of the first and second sections may be removable from the spacer member and replaced with an alternative replacement section in order to alter the flexibility characteristics of the spacer member. For example, in the embodiment illustrated in FIG. 3A, second section 56 may be removable from the spacer member 31. A plurality of replacement sections having flexibility characteristics different from the first section 54 and the second section 56 may be provided to replace the second section 56. It should be appreciated that both the second section 56 and the replacement sections may be engaged with the spacer member 31 and the first section 54 through any standard manner, including a friction fit, pinning, tacking, stapling, screwing and/or any combination thereof, just to name a few possibilities. In this form, the stabilization of the spinal motion segment may be monitored subsequent to positioning the spacer member 31 between the spinous processes $SP_1$, $SP_2$ to determine if alterations to the stabilization are desired. For example, it may be desired to adjust the positioning of one or both of the centers of rotation for flexion and extension $COR_F$, $COR_E$. When an alteration to the stabilization of the spinal motion segment is desired, the removable section may be replaced with one of the replacement sections having different flexibility characteristics. For example, in one non-limiting form, when it is desired to reposition the center of rotation for extension $COR_E$ in an anterior direction, the flexibility of the selected replacement section may be less than that of the second section 56 but greater than that of the first section 54. It should be appreciated that the stabilization of the spinal motion segment may be continually monitored and that the removable one of the first and second sections may be replaced with one of the replacement sections until the desired stabilization is achieved. The procedure of removing the removable section and replacing it with the alternative section may be performed through any standard surgical procedure. However, in one form, in order to minimize surgical complexity and trauma to the patient, it is contemplated that the procedure is performed percutaneously through a minimally invasive procedure.

Figure 4A:
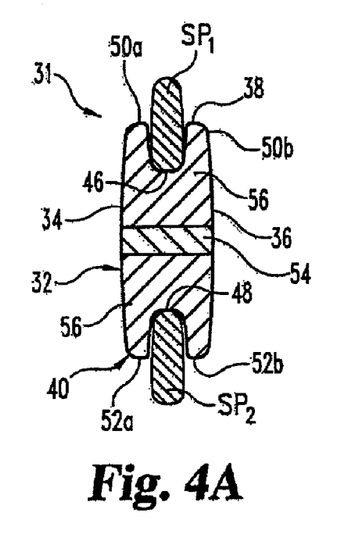
FIG. 4A is a sectional view of an alternative embodiment spacer member taken along a view plane corresponding to line 4-4 in FIG. 2.
Figure 4B:
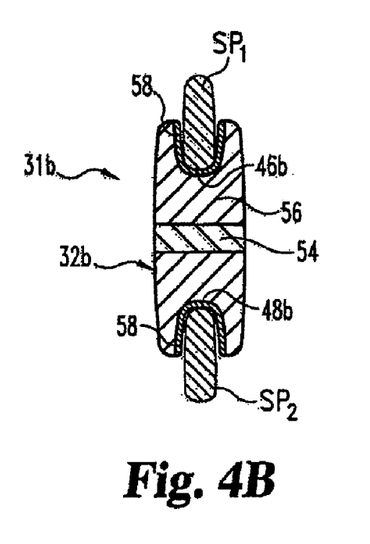
FIG. 4B is a sectional view of an alternative embodiment spacer member taken along a view plane corresponding to line 4-4 in FIG. 2.

Referring now to FIGS. 4A and 4B, wherein like numerals refer to like features previously described, there is shown a sectional view of respective spacer members 31 and 31b along line 4-4 of FIG. 2. In FIG. 4A, the portion of the body 32 of spacer member 31 which forms arms 50a, 50b, 52a, and 52b engages with the upper and lower spinous processes $SP_1$, $SP_2$. In one form, this portion of the body 32 may be flexible enough to at least partially conform to the spinous processes $SP_1$, $SP_2$. In an alternative embodiment such as spacer 31b, the third section 58 is disposed around the concave portions 46b, 48b to provide a surface that conforms to the spinous processes $SP_1$, $SP_2$ regardless of the flexibility or rigidity of the rest of the body 32b.

Figure 5:
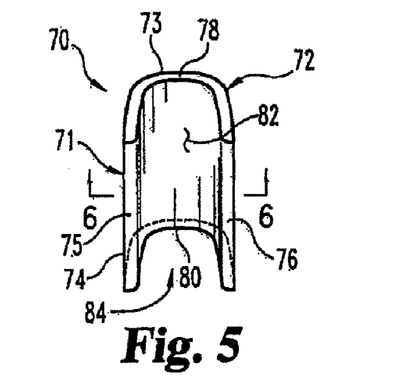
FIG. 5 is a perspective view of an alternative embodiment spacer member.

An alternative embodiment spinal implant 70 in the form of spacer member 71 is illustrated in perspective view in FIG. 5. The spacer member 71 includes a substantially U-shaped body 73 including longitudinal members 75 and 76 and an arcuate portion 82 extending between the longitudinal members 75, 76 to form a concave area 84 extending between surfaces 78 and 80. In an implantation orientation the body 72 is structured for positioning in the space S between the upper and lower spinous processes $SP_1$, $SP_2$ such that the concave area 84 faces in an anterior direction with the upright members 75, 76 abutting a posterior surface of the laminae 19a, 19b and the upper spinous process $SP_1$ engaging with surface 78 and the lower spinous process $SP_2$ engaging with surface 80. In one non-illustrated embodiment, the body 72 may be structured so that the longitudinal members 75, 76 may be positioned between the adjacent laminae 19a, 19b to keep a distraction space between the laminae 19a, 19b while the surfaces 78, 80 engage with and support the adjacent spinous processes $SP_1$, $SP_2$. In one or more forms, the body 72 may include one or more features structured to resist anterior migration of the implant 70 into the spinal canal. In yet another non-illustrated form, it is contemplated that surfaces 78, 80 may include a recessed area for receiving and engaging the spinous process $SP_1$, $SP_2$.

Figure 6:
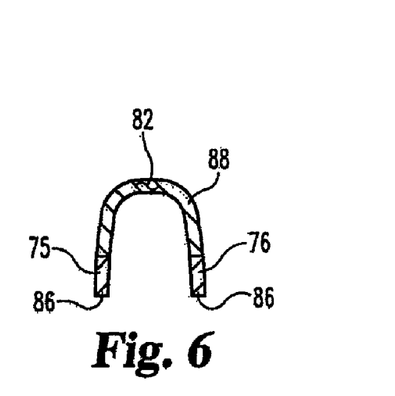
FIG. 6 is a sectional view taken along view line 6-6 in FIG. 5.

Referring to FIG. 6, there is shown a section view of the spacer member 71 along view line 6-6 of FIG. 5. In this form, spacer member 71 includes a first section 86 disposed generally in the longitudinal members 75, 76 and a second section 88 disposed generally in the arcuate portion 82. As described above in regard to spacer member 31, the spacer member 71 can be fabricated from components that are flexible or exhibit at least some flexibility with the second section 88 being more flexible than the first section 86. In one form, the flexibility of the sections 86, 88 may be varied by using materials with different elastic, flexibility, or rigidity qualities. It is further contemplated that one or more of the materials comprising sections 86, 88 may be selected from the materials set forth herein above in regard to spacer member 31. In the implantation orientation of spacer member 71, the more rigid first section 86 is positioned anterior to the more flexible second section 88 and the centers of rotation for flexion and extension $COR_F$, $COR_E$ will be repositioned relative to the normal center of rotation $COR_N$ as described above in regard to spacer member 31. Moreover, with the more rigid section 86 disposed generally in longitudinal members 75, 76, the spacer member 71 will maintain a distraction distance between the laminae 19a, 19b to help avoid stenosis and associated neural complications. While alternative section views of spacer member 71 have not been provided, it is contemplated that the configuration and positioning of the first section 86 and the second section 88 may be modified in order to provide a spacer member 71 with various flexibility and stabilization features.

Figure 7:
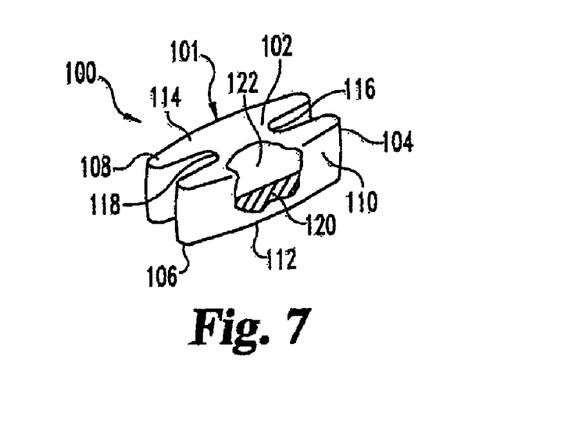
FIG. 7 is a perspective view in partial section of another embodiment spacer member.

An additional alternative embodiment spinal implant 100 in the form of spacer member 101 is illustrated in perspective view in FIG. 7. Spacer member 101 is generally similar to spacer member 31 and includes a body 102 which in an implantation orientation extends between a superior end 104 and an inferior end 106. The body 102 also generally includes lateral sides 108, 110 and anterior side 112 and posterior side 114. The concave portions 116, 118 are structured to engage with and receive the upper and lower spinous processes $SP_1$, $SP_2$ as described herein. In the illustrated form, the body includes a first section 120 positioned anterior to a hollow chamber 122 with the chamber 122 being structured to receive one or more injectable materials. When the chamber 122 includes the injectable material, the body 102 includes a second section in addition to the first section 120. The injectable material may include gels, pastes, slurries, or liquids, just to name a few possibilities. In one form, the injectable material may be deliverable in a first state and cure to a second state after injection. However, regardless of the form, the injectable material will be more flexible than the first section 120 in order to provide an implant with flexibility and stabilization features similar to that of spacer member 31. In one non-illustrated form, the body 102 may include one or more injection ports to receive the injectable material from a delivery instrument. In yet another form, it is contemplated that the body 102 may include one or more chambers in addition to chamber 122. It should also be appreciated that the positioning of the one or more chambers 122 or first section 120 may be altered to provide spacer members with various flexibility and stabilization features. Moreover, it is contemplated that section 120 may be the more flexible section and that the more rigid material may be delivered to the one or more chambers 122.

In another form, it is contemplated that the injectable material may be removed from the chamber 122 subsequent to positioning of the spacer member 101 at an implantation location. In this form, a patient may be monitored to determine if changes to the stabilization of the spinal motion segment are necessary. For example, after the initial positioning of the spacer member 101, it may be determined that one or both of the centers of rotation for flexion and extension $COR_F$, $COR_E$ needs to be adjusted. If an adjustment is necessary, the injectable material may be removed and replaced with an alternative injectable material having different flexibility characteristics in order to alter one or both of the centers of rotation for flexion and extension $COR_F$, $COR_E$ as desired. It is further contemplated that the stabilization of the spinal motion segment may be continuously monitored and, if necessary, the injectable material may be varied until desired stabilization of the spinal motion segment is accomplished. The injectable material may be removed and introduced to the chamber 122 of the spacer member 101 through any known surgical procedure. In one form however, the spacer member 101 is structured for access by a delivery instrument through a percutaneous surgical procedure in a minimally invasive manner in order to minimize surgical complexity and trauma to the patient.

Figure 8:
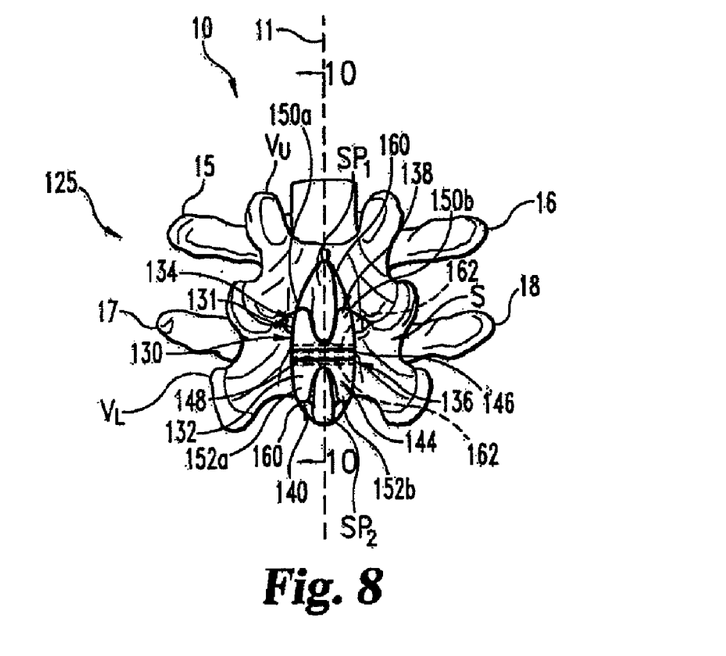
FIG. 8 is an elevation view of the posterior portion of the spinal column motion segment of FIG. 1 with a spacer member assembly including a tethering system engaged therewith.
Figure 9:
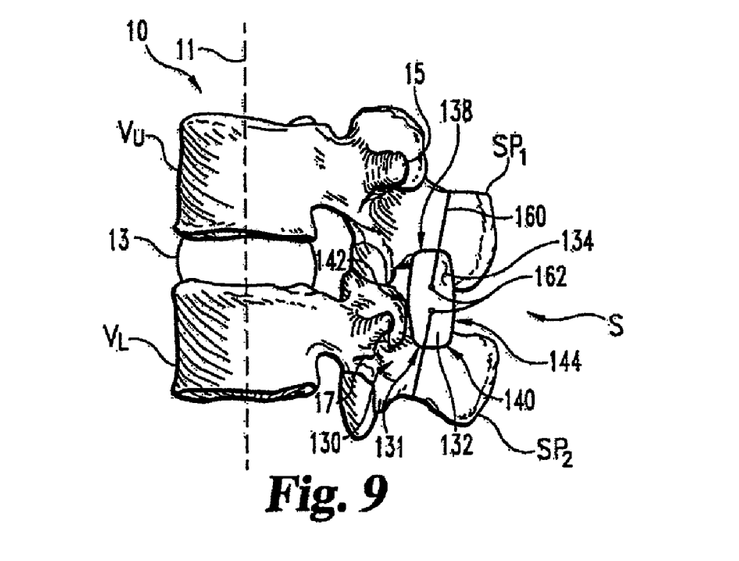
FIG. 9 is a lateral view of the spinal column motion segment and spacer member assembly of FIG. 8.

Referring now to FIGS. 8 and 9, there is shown an implant assembly 125 relative to the spinal motion segment of FIGS. 1 and 2. Implant assembly 125 includes a spinal implant 130 in the form of a spacer member 131 positioned in the space S and extending between and engaging with the spinous processes $SP_1$, $SP_2$ to provide stabilization and modification of the spinal motion segment. Spacer member 131 includes a body 132 which in its implanted orientation has a first lateral side 134 and a second lateral side 136, with the lateral sides 134, 136 extending between a superior end 138 and an inferior end 140. As best seen in FIG. 9, for example, the body also includes an anterior side 142 opposite a posterior side 144. It should be appreciated that the transition between each of the anterior and posterior sides 142, 144, lateral sides 134, 136, and superior and inferior ends 138, 140 may be rounded or beveled in order to decrease the profile of the body 132 and minimize intrusion and the potential for trauma to adjacent neural tissue and surrounding spinal anatomy.

The body 132 further includes a first concave portion 146 and a second concave portion 148 situated at respective superior and inferior ends 138, 140. Each of the concave portions 146, 148 is disposed between a pair of respective upright arms 150a, 150b and 152a, 152b. Concave portions 146, 148 are sized and shaped to engage with and receive respective inferior surface 12 of the upper spinous process $SP_1$ and superior surface 14 of the lower spinous process $SP_2$. The arms 150a, 150b, 152a, and 152b extend beyond the respective concave portion 146 and concave portion 148 to engage with the lateral sides of the spinous processes $SP_1$, $SP_2$ to prevent or resist dislodgement of the spacer member 131 from space S.

Spacer member 131 is similar to spacer member 31 discussed above but also includes an engaging member 160 extending therefrom to attach spacer member 131 to posterior vertebral elements or implants of the spinal motion segment. Spacer member 131 includes any arrangement for spacer member 31 discussed above in FIGS. 1-3G. Spacer member 131 includes through-passages 162 extending between opposite sides thereof, which include the lateral sides 134, 136 of spacer member 131 in the illustrated embodiment. Passages 162 receive engaging member 160 therethrough. Engaging member 160 may comprise multiple engaging members, or a single engaging member looped through passages 162. Still other embodiments contemplate a single passage 162, or three or more passages 162, through which one or more engaging members 160 are positioned.

Figure 10A:
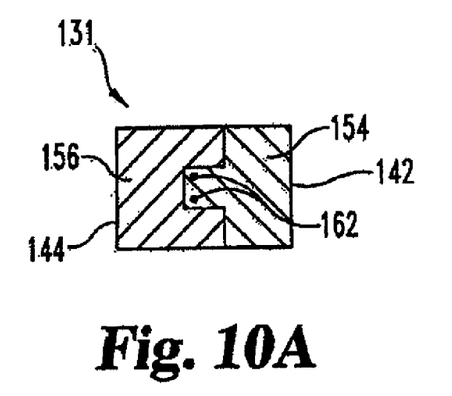
FIGS. 10A-10C are sectional views taken along view line 10-10 in FIG. 8 of various alternative embodiment spacer members.
Figure 10B:
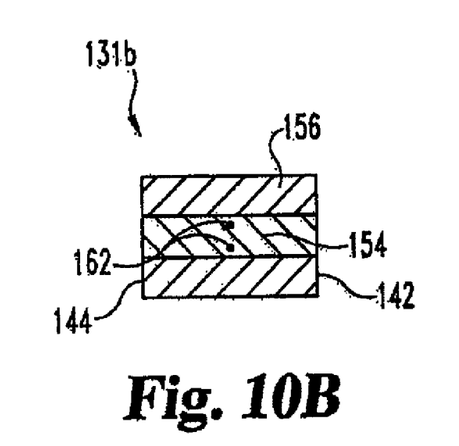
Figure 10C:
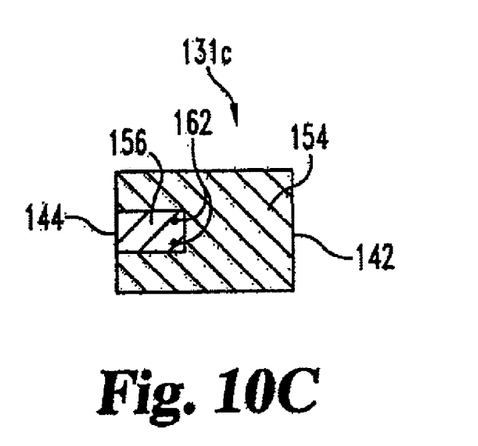

Referring to FIG. 10A there is illustrated a section view of spacer member 131 along view line 10-10 of FIG. 8. As indicated, spacer member 131 is similar to spacer member 31 and likewise includes a first section 154 and a more flexible second portion 156. Sections 154, 156 are also similar to sections 54, 56 described above in regard to spacer 31. However, the first section 154 includes passages 162 extending therethrough. When the engaging member 160 is received in passages 162 and is engaged to posterior vertebral elements or other implants and an axial pulling force is exerted on the spacer member 131, the more rigid section 154 resists deformation of the spacer body. Moreover, alternative embodiment spacer members 131b and 131c are illustrated in section view in FIGS. 10B and 10C. In FIG. 10B, the passages extend through the more rigid section 154 such that as an axial pulling force is exerted on the spacer member 131b, the more rigid section 154 again resists deformation of the spacer member 131b. In FIG. 10C, the passages 162 extend through the more flexible second section 156 which is situated between superior and inferior portions of first section 154. In this form, the second section 156 is deformable in response to the axial pulling force until it is limited by the surrounding more rigid first section 154. It should be appreciated that the engaging member 160 and the passages 162 may be alternatively configured relative to the first and second sections 154, 156 in accordance with the various embodiments set forth herein.

Engaging member 160 can be in the form of a tether, cord, wire, cable, suture, band, strap, belt, or other suitable structure for manipulation and securement to one or more posterior vertebral elements. Engaging member 160 may be wrapped or positioned around posterior vertebral elements and then maintained in position with a crimp or other suitable fastener. Furthermore, engaging member 160 can be coupled to spacer member 131 in any suitable manner. In one embodiment, engaging member 160 is movably coupled to spacer member 131. Engaging member 160 can be integrally formed with spacer member 131, or can be attached by a fastener, suture, anchor, cable, link, over-molding or other suitable connection. Spacer member 131 can be provided with ears, eyelets, recesses or other suitable structure to facilitate engagement of engaging member 160 to spacer member 131. Engaging member 160 may be employed in spinal stabilization procedures where it is desired to limit spinal flexion by, for example, wrapping engaging member 160 about the superior surface of the upper spinous process and/or upper lamina and the inferior surface of the lower spinous process and/or the lower lamina. Engaging member may alternatively be employed as a retention mechanism to maintain spacer member 160 in position between the spinous processes.

With respect to the various embodiments described herein, the engaging member can be joined or fixed to the spacer member using various devices and/or techniques, or can be integrally formed with or form an extension of the spacer member. The spacer member can be joined or attached to the engaging member by, for example, sewing the engaging member to the spacer member, thermal welding or bonding, adhesive bonding, three dimensional weaving or braiding, screws, staples, pins, tacks or rivet fixation. Furthermore, the engaging member can be secured to the spacer member either before or after the spacing member is placed between the spinous processes. The engaging member can be engaged to other engaging members of other implant assemblies or to other implants engaged to the spinal column in the surgical procedure.

The engaging members described herein can be made from any one or combinations of biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, and combinations thereof.

While not illustrated, it should be appreciated that one or more of the spacers contemplated herein may include one or more additional sections with one more additional elasticity, flexibility, or rigidity qualities. Moreover, in another non-illustrated form, it is contemplated that upon implantation the spacer member may not include one of the first or second sections. In this form, a plurality of coupleable members sized and shaped like the first or second section may be provided with differing flexibility characteristics so that a surgeon may select which to include at the implant site during a surgical procedure. It should be appreciated that the coupleable members may engage with the spacer members through any one or more of a press fit engagement, a mechanical connection, fusion, or adhesion, just to name a few possibilities. It should also be appreciated that in one or more forms the spacer members may be integrally formed or may include one or more portions coupled together.

In a further embodiment, it is contemplated that stiffening members can be provided to enhance or increase the stiffness of spacer members 31, 71, 101, 131. For example, in one non-illustrated form, a stiffening member may be in the form of a band that extends about and contacts the perimeter of spacer members 31, 71, 101, 131. Moreover, more than one stiffening member can be provided about spacer members 31, 71, 101, 131 to allow the stiffness profile of the spacer members 31, 71, 101, 131 to be increased or decreased by adding or removing a stiffening member. Examples of suitable stiffening members include woven fabric tubing, woven and nonwoven mesh, or braided or woven structures, sutures, tethers, cords, planar members, bands, wires, cables, or any other component capable of extending about the perimeter of the spacer member to increase stiffness thereof.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A spinal implant, comprising:
a spacer comprising a body having opposite upper and lower ends and structured for positioning in an interspinous gap between adjacent upper and lower spinous processes of a human spinal motion segment;
the upper end structured to contact an inferior surface of the upper spinous process of the human spinal motion segment and the lower end structured to contact a superior surface of the lower spinous process of the spinal motion segment, wherein each of the upper and lower ends includes a concave portion sized and shaped to receive one of the respective upper and lower spinous processes and the concave portions are each disposed between a pair arms extending from the upper and lower surfaces, respectively, to engage with lateral surfaces of the spinous processes;
the body comprising at least distinctive first and second sections forming an asymmetrical stiffness profile that varies between anterior and posterior sides of the spacer; wherein the first and second sections have flexibility characteristics that differ from one another, wherein one of the flexibility characteristics relates to a modulus of elasticity and wherein the second section has a smaller modulus of elasticity than the first section;
wherein the anterior side defines the anterior extent of the spacer and the posterior side defines the posterior extent of the spacer;
wherein the anterior side and the posterior side each extends from the upper end to the lower end; wherein the second section is positioned between the first section and the posterior side;
wherein the spacer includes a first lateral exterior side and a second lateral exterior side, each lateral side extending from the upper end to the lower end; wherein the first section extends along the anterior side and the first and second lateral sides and the second section extends along the posterior side and the first and second lateral sides;
wherein the spacer is configured such that, when the spacer is disposed both in the interspinous gap between the upper and lower spinous processes and external to a disc space defined by and between corresponding vertebral bodies so as to moveably support the upper and lower spinous processes, the spacer modifies a center of rotation of the vertebral bodies relative to each other in at least one of spinal extension and spinal flexion.

2. The implant of claim 1 wherein the first section includes a first material and the second section includes a second material; wherein the second material is more flexible than the first material.

3. The implant of claim 1 wherein each of the arms are congruent with either the first or second lateral sides of the body.

4. The implant of claim 1 further comprising at least one tether engaged to the body and extending therefrom, the tether being engageable with at least one of the upper and lower spinous processes.

5. The implant of claim 4 wherein the at least one tether extends through the first section and wherein the first section is more rigid than the second section.

6. The implant of claim 5 wherein the first section includes a bore extending therethrough between opposite sides of the body transversely to a direction between the upper and lower ends, with the tether extending through the bore.

7. The implant of claim 4 wherein the at least one tether extends through the second section of the body, the second section being less rigid than the first section and being at least partially surrounded by the first section.

8. A method for stabilizing a spinal motion segment, comprising:
providing a spacer as set forth in claim 1;
adjusting a center of rotation of a spinal motion segment in at least one of spinal extension and spinal flexion by positioning the spacer in an interspinous gap defined between adjacent upper and lower spinous processes of the spinal motion segment with:
the first section oriented anteriorly of the second section; such that at least a portion of the second section is disposed posteriorly of a posterior-most point of the first section;
the first and second sections movably supporting the upper and lower spinous processes;
the spacer disposed entirely external to a disc space defined by and between vertebral bodies corresponding to the upper and lower spinous processes.

9. The method of claim 8 wherein the spacer varies the center of rotation for both spinal flexion and spinal extension.

10. The method of claim 8 wherein the positioning comprises positioning the spacer in the interspinous gap such that both the first and second sections directly contact the upper and lower spinous processes.

11. The method of claim 8 further comprising affixing the spacer to posterior vertebral elements of the spinal motion segment with a tether.

12. The method of claim 8 wherein the positioning comprises positioning the spacer in the interspinous gap such that the second section is disposed entirely posteriorly of the first section.

13. The method of claim 8 further comprising removably mounting the second section to the first section prior to the positioning the spacer in the interspinous gap.

* * * * *